(12) United States Patent
Moe et al.

(10) Patent No.: US 9,962,230 B2
(45) Date of Patent: May 8, 2018

(54) INSTRUMENT ORGANIZATION SYSTEMS AND ASSOCIATED METHODS

(71) Applicant: University of Washington through its Center for Commercialization, Seattle, WA (US)

(72) Inventors: Kristen S. Moe, Seattle, WA (US); Randall Bly, Seattle, WA (US); Blake Hannaford, Seattle, WA (US)

(73) Assignee: University of Washington, Seattle, WA (US)

( * ) Notice: Subject to any disclaimer, the term of this patent is extended or adjusted under 35 U.S.C. 154(b) by 123 days.

(21) Appl. No.: 14/435,569

(22) PCT Filed: Nov. 18, 2013

(86) PCT No.: PCT/US2013/070633
§ 371 (c)(1),
(2) Date: Apr. 14, 2015

(87) PCT Pub. No.: WO2014/078817
PCT Pub. Date: May 22, 2014

(65) Prior Publication Data
US 2015/0297295 A1  Oct. 22, 2015

Related U.S. Application Data

(60) Provisional application No. 61/727,256, filed on Nov. 16, 2012.

(51) Int. Cl.
*A61B 19/02* (2006.01)
*A61B 50/13* (2016.01)
(Continued)

(52) U.S. Cl.
CPC .............. *A61B 50/13* (2016.02); *A61B 50/00* (2016.02); *A61B 50/20* (2016.02); *A61B 50/24* (2016.02); *A61B 50/26* (2016.02)

(58) Field of Classification Search
CPC ......... A61B 50/00; A61B 50/13; A61B 50/15; A61B 50/22; A61B 50/24;
(Continued)

(56) References Cited

U.S. PATENT DOCUMENTS 5,010,899 A * 4/1991 Thompson ............. A61B 46/23
128/849
5,518,310 A * 5/1996 Ellman ................ A61G 12/001
312/209

(Continued)

FOREIGN PATENT DOCUMENTS

JP  2009537233 A  10/2009
WO  9714904 A1  4/1997
(Continued)

*Primary Examiner* — Michael Safavi
(74) *Attorney, Agent, or Firm* — Perkins Coie LLP

(57) ABSTRACT

Organization systems for surgical instruments and associated methods and systems are disclosed herein. In one embodiment, a surgical instrument organization system can be configured for use in a medical environment, and can include a flexible, sterile container having a lower portion. The container can include an attachment system configured to elastically couple one or more surgical instruments to the lower portion of the container. In some embodiments, the container can be carried by a portable base coupled to a platform via an adjustable support member.

14 Claims, 9 Drawing Sheets

(51) Int. Cl.
*A61B 50/26* (2016.01)
*A61B 50/00* (2016.01)
*A61B 50/20* (2016.01)
*A61B 50/24* (2016.01)

(58) Field of Classification Search
CPC ........ A61B 2050/105; A61B 2050/155; A61B 50/20; A61B 50/10; A61B 2050/005
See application file for complete search history.

(56) References Cited

U.S. PATENT DOCUMENTS

| | | | | |
|---|---|---|---|---|
| 8,568,391 | B2* | 10/2013 | Kerns | A61B 50/33 235/435 |
| 2002/0092816 | A1* | 7/2002 | Kim | F16L 3/223 211/85.13 |
| 2005/0208451 | A1* | 9/2005 | Johnstone | A61G 15/18 433/78 |
| 2007/0107130 | A1* | 5/2007 | Elhabashy | A61B 50/20 5/622 |
| 2007/0246613 | A1 | 10/2007 | Kennedy et al. | |
| 2010/0152589 | A1* | 6/2010 | Asai | A61B 8/00 600/459 |
| 2011/0084039 | A1 | 4/2011 | Walters et al. | |
| 2012/0227751 | A1* | 9/2012 | Horer | A61M 25/02 128/852 |
| 2012/0325704 | A1* | 12/2012 | Kerns | A61B 50/33 206/370 |

FOREIGN PATENT DOCUMENTS

| | | | | |
|---|---|---|---|---|
| WO | | 9904190 | A1 | 1/1999 |
| WO | | 2006007699 | A1 | 1/2006 |
| WO | | 2007136820 | A2 | 11/2007 |
| WO | | 2011097072 | A1 | 8/2011 |
| WO | WO 2012151062 | * | 11/2012 | ............. A61B 50/33 |

* cited by examiner

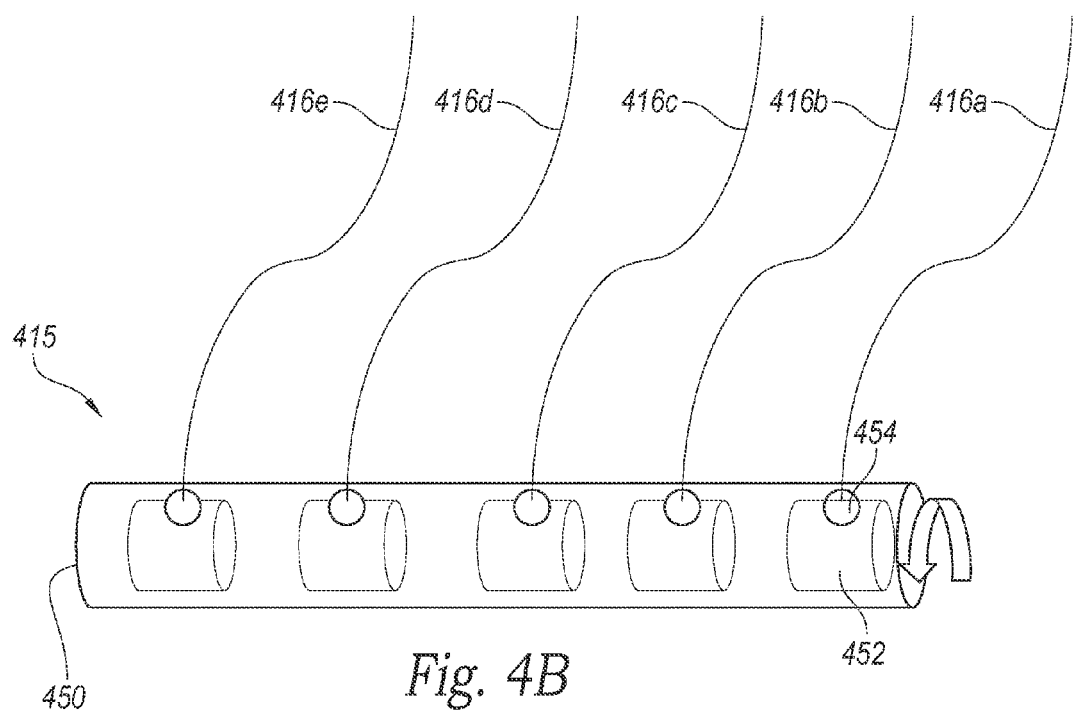

INSTRUMENT ORGANIZATION SYSTEMS AND ASSOCIATED METHODS

CROSS-REFERENCE TO RELATED APPLICATION(S)

This application claims the benefit of U.S. Provisional Application No. 61/727,256, filed Nov. 16, 2012, and incorporated herein by reference in its entirety.

TECHNICAL FIELD

The present technology relates generally to systems and methods for organizing instruments. In particular, several embodiments are directed to systems configured to organize instruments (e.g., surgical instruments, cables, cords, etc.) for use in, for example, hospital rooms and/or other medical operating environments.

BACKGROUND

Many surgical operations require multiple surgical devices (e.g., endoscopes, microdebriders, sonopets, coblators) attached to one or more surgical instruments or consoles via cables (e.g., power cables, fiber-optic cables, electrical cables, cords, tubes, hoses, conduits, wires). During an operation, surgical devices can be arranged near one another (e.g., on a surgical stand near an operating table, on a portion of a patient's body) such that they are readily accessible to a doctor. As a result, however, cables attached to the devices often wind up lying next to and/or on top of each other. The cables can become tangled such that the use of one device may inadvertently cause one or more other unsecured devices to move, potentially falling onto the floor. The tanglement of cables can also inhibit quick access to such devices, which is often necessary during many surgical procedures. Accordingly, there exists a need for a system to organize surgical instruments and/or cables in a medical environment.

BRIEF DESCRIPTION OF THE DRAWINGS

FIG. 4B is an enlarged view of a portion of FIG. 4A.

DETAILED DESCRIPTION

Figure 1A:
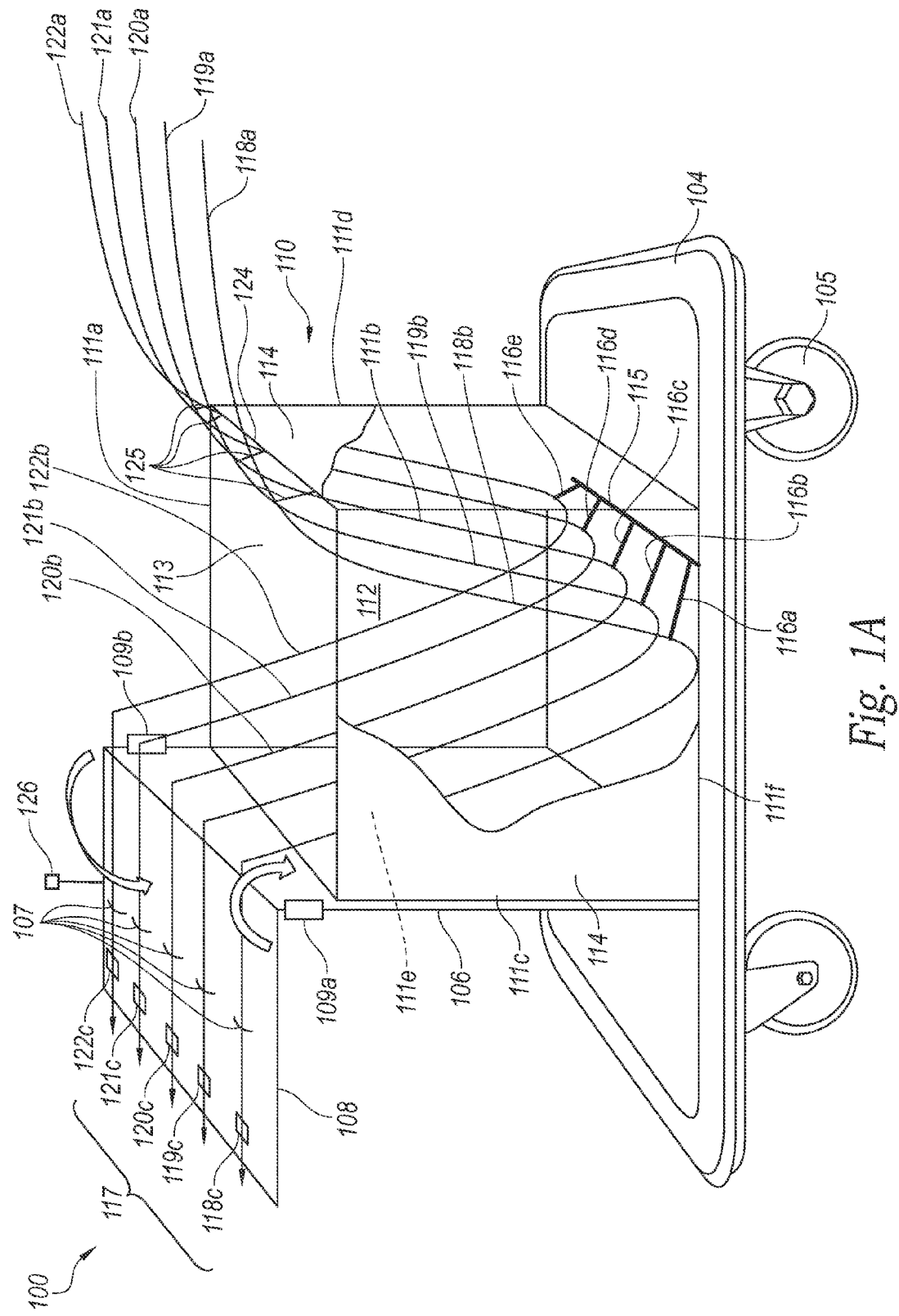
FIG. 1A is a partially schematic isometric view of an instrument organization system configured in accordance with embodiments of the present technology.

The present technology relates generally to instrument organization systems and associated methods. In one aspect of the present technology, a surgical instrument organization system may include a support member fixedly attached to a base, and a platform operably coupled to the support member. A container attached to the base and the support member can be configured to receive a plurality of surgical instruments (e.g., surgical tools, cables, cords, conduits, hoses, wires, tubes). The container can include an attachment system configured to operably couple surgical instruments to a lower portion of the container. In one embodiment, the container can comprise a flexible, sterile container configured to receive intermediate portions of the plurality of surgical instruments. In another embodiment, the container can comprise rigid, sterile container that includes a framework having a lower portion and a plurality of side portions. The framework can define a space through which intermediate portions of the plurality of surgical instruments are received. In some embodiments, the attachment system can include a plurality of tethers with individual tethers being configured to elastically attach corresponding surgical instruments to the container. In some other embodiments, the attachment system can also include, for example, a plurality of retractors. A first end of individual tethers can be attached to a surgical instrument, and a second end of individual tethers can be attached to and at least partially wound around a corresponding retractor.

In another aspect of the present technology, a surgical tool organization system includes a flexible, sterile container having a lower portion. The container may be configured to receive two or more surgical tools. The container can also include an attachment system configured to elastically couple surgical tools to the lower portion of the container. In some embodiments, the container may be carried by a portable base. An adjustable support member can couple the base to a platform. The support member can be configured to move the platform between a first height and at least a second height and/or tilt the platform (e.g., vertically or horizontally) between a first angle and a second angle. The platform can include, for example, a plurality of fasteners positioned to releasably secure proximal portions of corresponding surgical tools to the platform. In some other embodiments, the attachment system can comprise a plurality of tethers configured to elastically attach corresponding surgical tools to the container. The individual tethers can have, for example, an adjustable elasticity such that a user can adjust the elasticity of the individual tethers. In further embodiments, the organization system can also include a support arm configured to be attached to a room surface and extend therefrom. The container can be configured to be operably coupled to the support arm.

In yet another aspect of the present technology, a surgical instrument organization system includes a flexible, sterile container that includes an attachment system configured to retractably secure one or more surgical instruments to a lower portion of the container. A portable base configured to carry the container can be coupled to a platform via an adjustable support member. The support member is configured to move the platform between a first height and at least a second height. In one embodiment, independently-adjustable first and second coupling devices can couple the platform to the support member. The coupling devices can be configured to allow a user to adjust an orientation of the platform relative to the base from a first angle to at least a second angle in a first direction. In some embodiments, the coupling devices can also be configured to allow a user to adjust the orientation of the platform relative to the base from a third angle to at least a fourth angle in a second direction different from the first direction. In some other embodiments, the organization system can include a light (e.g., LED light, an optical fiber, a bundle of optical fibers) and/or any suitable means for illuminating an interior portion of the container and/or the platform.

Certain specific details are set forth in the following description and in FIGS. 1A-6 to provide a thorough understanding of various embodiments of the technology. Other details describing well-known structures and systems often associated with surgical instruments and organization systems thereof have not been set forth in the following technology to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1A-6.

FIG. 1A is a partially schematic isometric view of a cord organization system 100 configured in accordance with embodiments of the present technology. The cord organization system 100 includes a base 104 comprising a plurality of movers 105 (e.g., wheels, rollers, casters). A platform 108 is coupled to the base 104 by a support structure or support member 106 attached thereto. The platform 108 includes a plurality of fasteners 107 arranged along the platform 108 and configured to attach or otherwise secure individual surgical tools/instruments to the platform 108. The fasteners 107 can include, for example, hooks, cables, elastic bands, Velcro strips, and/or any other suitable fasteners. A pair of coupling devices or connectors 109 (shown individually as a first connector 109a and a second connector 109b) operably couple the platform 108 to the support member 106. The connectors 109, for example, can be configured to allow an operator to adjust an orientation of the platform 108 relative to the base 104 from a first angle to at least a second angle in a first direction. In some embodiments, the connectors 109 can also be configured to allow a user to adjust the orientation of the platform 108 relative to the base 104 from a third angle to at least a fourth angle in a second direction different from the first direction. Moreover, while the embodiment illustrated in FIG. 1A shows the platform 108, in other embodiments, one or more additional platforms may be included with the system 100. Additional platforms can be attached, for example, at any suitable location in and/or on the system 100 (e.g., at a location along the base 104) and can be adjusted and/or fixed at any suitable user-desired height (e.g., substantially the same height as a patient on an operating surface).

A container 110 is carried by the base 104, and is attached or otherwise secured to the support member 106. The container 110 includes, for example, a plurality of side portions 111 (shown individually as an upper portion 111a, a first side portion 111b, a second side portion 111c, a third side portion 111d, a fourth side portion 111e and a lower portion 111f). The side portions 111 define a cavity or a space 112 that can receive one or more surgical tools or instruments 117 (e.g., surgical tools, cables, cords, wires, hoses, tubes, conduits) entering the container 110 via an aperture 113 proximate the upper portion 111a.

In some embodiments, the container 110 can also include an illumination source 126 (e.g., one or more light bulbs, liquid emitting diodes (LEDs), optical fibers) configured to illuminate at least a portion of the container 110 and/or the platform 108. The container 110 and/or the platform 108 can include, for example, a structure (not shown) configured to hold the illumination source 125 and direct light in a desired direction (e.g., toward the platform 108 and/or toward the surgical tools/instruments 117 in the space 112).

The container 110 further comprises a barrier 114 (e.g., sterile drape, a sterile bag, sterile sheets) made of, for example, polyethylene, nylon, rayon, polyester or any suitable sterile barrier material. In some embodiments, for example, the container 110 can be configured as a rigid structure and the side portions 111 can comprise a rectangular framework of support structures and/or sidewalls configured to receive the barrier 114. In other embodiments, for example, the container 110 can be configured as a flexible, sterile container (e.g., a flexible, sterile bag) comprising the barrier 114 and the side portions 111, which can be configured as flexible side portions of the container 110. The upper portion 111a, for example, can be adjusted by an operator to increase or decrease an area of the aperture 113 based on, for example, a number of the instruments 117 passing therethrough. In further embodiments, as discussed below in reference to FIG. 4A, the container 110 can comprise any suitable shape and material. Moreover, in the embodiment shown in FIG. 1A, the container 110 is attached or otherwise coupled to the base 104 and the support member 106. In other embodiments, however, the container 110 can be utilized without one or both of the base 104 and the support member 106.

The surgical tools/instruments 117 can include a first instrument 118 (e.g., a surgical tool, cable, cord, wire, hose, tube, conduit) shown as a distal portion 118a, an intermediate portion 118b, and a proximal portion 118c. The surgical tools/instruments 117 (e.g., a surgical tool, cable, cord, wire, hose, tube, conduit) can also include second, third, fourth and fifth instruments 119, 120, 121, 122, respectively each shown as a distal portion (119a, 120a 121a and 122a, respectively), an intermediate portion (119b, 120b, 121b and 122b, respectively), and a proximal portion (119c, 120c, 121c, and 122c, respectively). The distal portions 118a, 119a, 120a, 121a, and 122a can be coupled or otherwise connected to first, second, third, fourth and fifth medical components or consoles, respectively (not shown). As those of ordinary skill in the art will appreciate, the medical components or consoles can include, for example, computers, displays, electrical current sources (e.g., power supplies), liquid sources (e.g., a water supply), gas sources, waste disposal components and/or any suitable operating room component. The proximal portions 118c, 119c, 120c, 121c and 122c of the corresponding surgical tools/instruments can be coupled to or otherwise connected to any suitable surgical device, instrument or tool (not shown) such as, for example, an endoscope, a microdebrider, a suction, a suction cautery, a bipolar cautery, a sonopet, a coblator, etc.

As noted above, the container 110 is configured to receive at least a portion of the individual surgical tools/instruments 117. More specifically, a fastening system 124 at the upper portion 111a proximate the aperture 113 includes a plurality of fasteners 125 (e.g., hooks, clamps, Velcro strips, clips, cable ties, cable loops, carabiners) configured to secure or otherwise attach the surgical tools/instruments 117 to prevent unsterile portions (e.g., the distal portions 118a-122a) from entering the sterile space 112 of the container 110. Furthermore, an attachment system 115, positioned, for example, within the container 110, is configured to attach, couple, connect, or otherwise releasably secure individual surgical tools/instruments 117 to the container 110. In the embodiment illustrated in FIG. 1A, the attachment system 115 is shown disposed at the lower portion 111f of the container 110. In other embodiments, however, the attachment system 115 may be positioned at any suitable location within the container 110. In some embodiments, the attachment system 115 may be disposed, for example, at the upper portion 111*a* of the container (e.g., proximate the platform 108). In further embodiments, the attachment system 115 may be located at a position external to the container 110 (e.g., at a location on the base 104.)

The attachment system 115 can include a plurality of fasteners, straps or tethers 116 (shown individually as a first tether 116*a*, a second tether 116*b*, a third tether 116*c*, a fourth tether 116*d*, and a fifth tether 116*e*). Individual tethers 116 can be attached to corresponding surgical tools/instruments 117 using a fastener such as, for example, a hook, a clamp, a Velcro strip, a clip, a cable tie, a cable loop, a carabiner, and/or one or more magnets. In some embodiments, the tethers 116 can be made of any suitable elastic material (e.g., rubber, neoprene, an elastomeric material). In other embodiments, however, the tethers 116 may be made of a flexible, inelastic material (e.g., an adjustable fabric strap, a rope). Moreover, in embodiments in which the tethers 116 are included in an attachment system in an interior portion of the container 110 (e.g., the attachment system 115), the tethers 116 may be made comprise one or more sterile materials. In other embodiments, however, in which the tethers 116 are included in an external attachment system (not shown), the tethers 116 may comprise sterile and/or non-sterile materials.

Figure 1B:
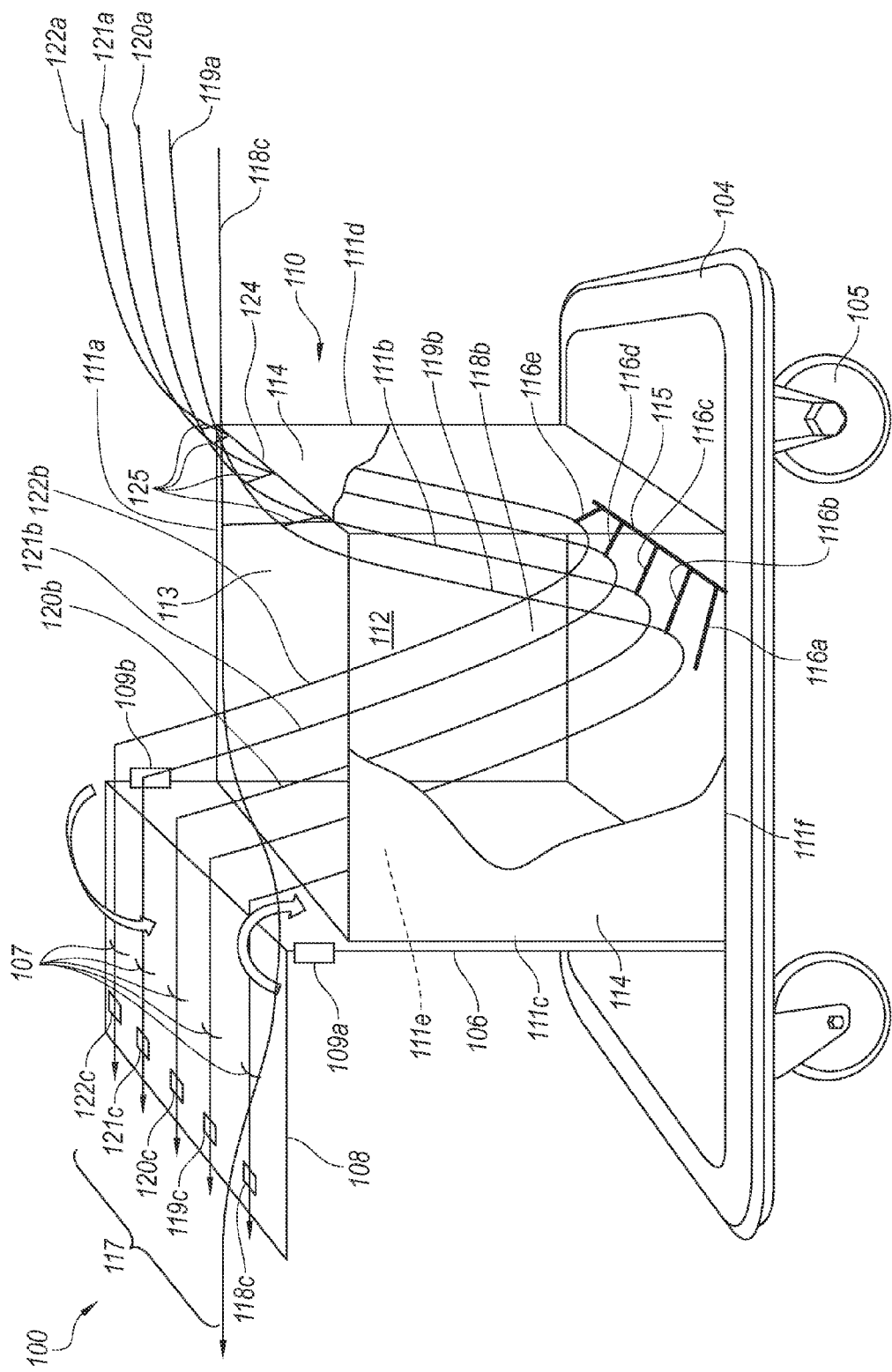
FIG. 1B is partially schematic isometric view of the organization system of FIG. 1A showing an instrument in an extended mode.

The tethers 116 can be configured to retain at least a portion of corresponding surgical tools/instruments 117 within or at least proximate the container 110, thus maintaining sterility of the instruments 117. FIG. 1A shows, for example, the first instrument 118 in a first mode (e.g., an inactive mode) in which the intermediate portion 118*b* is at least partially in the container 110. FIG. 1B, however, shows the first instrument 118 in a second mode (e.g., an active mode) in which a portion the first instrument 118 (e.g., the proximal portion 118*c*) has been pulled or otherwise moved (e.g., by an operator picking up and moving a device coupled to the proximal portion 118*c*). As shown in FIG. 1B, the first tether 116*a* can stretch or otherwise elongate to accommodate the movement of the first instrument 118 while maintaining the intermediate portion at least proximate the container 110. In some embodiments, the tethers 116 can be configured to have an adjustable tension or elasticity, thereby allowing an operator to adjust an elastic force of individual tethers 116 attached to corresponding surgical tools/instruments 117.

In some embodiments (not shown), the tethers 116 may comprise one or more weighted bodies. Individual weighted bodies (e.g., one or more sterilizable metal bodies) may be fastened (e.g., using hooks and/or pulleys) to corresponding surgical tools/instruments 117. A movement of one of the surgical tools/instruments 117 (e.g., extension of one of the surgical tools/instruments 117 during use by an operator) can be counteracted, for example, by a substantially opposite force (e.g., force of gravity) thereby causing the surgical tools/instruments 117 to retract into the container 100 when released by the operator. The use of weighted bodies as described above can provide an advantage of an application of a constant force (e.g., a gravitational force that does not change with distance). In some embodiments, the weighted bodies may be used with one or more of the tethers 116 within a sterile container (e.g., the container 110). In other embodiments, however, the weighted bodies may be implemented in an attachment system external to the container 110. In the latter case, one or weights can be disposed, for example, in vertical tracks (e.g., in one or more tracks or rails substantially parallel to the support member 106) external to the container 110 and can be fastened or otherwise attached (e.g., by a system of pulleys) to corresponding surgical tools/instruments proximate and/or within the container 110.

Figure 2:
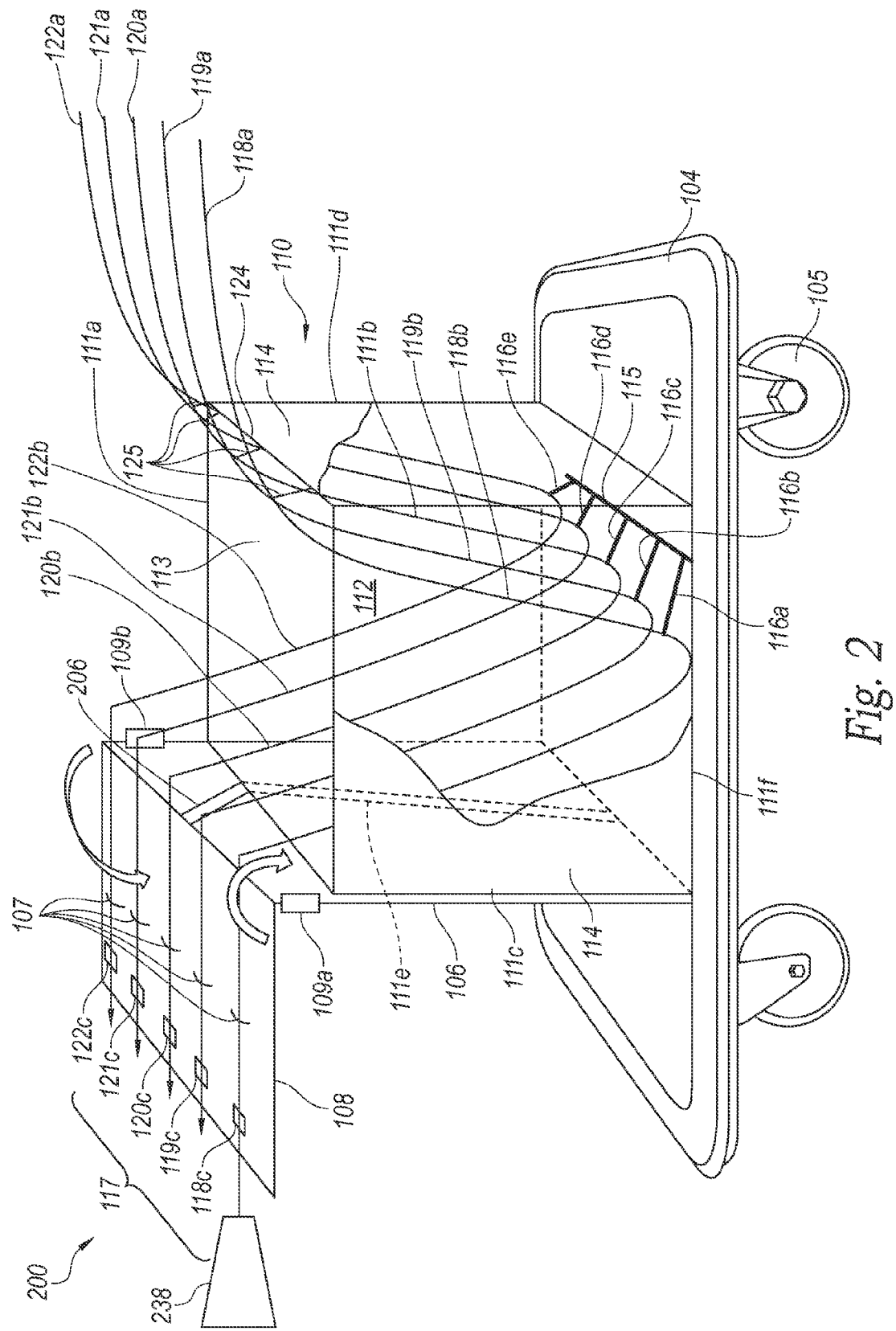
FIG. 2 is a partially schematic isometric view of an instrument organization system configured in accordance with another embodiment of the present technology.

FIG. 2 is a partially schematic isometric view of an instrument organization system 200 configured in accordance with another embodiment of the disclosed technology. In the illustrated embodiment, the platform 108 is coupled to the container 110 via a support arm 206. The platform 108 can be attached to the support arm 206 using any suitable attachment device (e.g., a ball joint, a hinge, one or more screws). In some embodiments, for example, the support arm 206 can be configured to allow the platform 108 to be moved and/or rotated in one of several directions. For example, the support arm 206 can be configured to move the platform between a first height (e.g., proximate the upper portion 111*a* of the container 110) and a second height (e.g., the height of surgical operating table).

In the embodiment illustrated in FIG. 2, a receiving cavity or duct 238 can be disposed proximate the platform 108 and can receive, for example, the proximal portion 118*c* of the first instrument 118 and can be configured, for example to prevent damage thereto. In some embodiments, the platform 108 may include one or more channels (no shown) configured to receive one or more corresponding instruments 117 (e.g., an endoscope) having, for example, heated end portions. The channels can allow the heated end portions to rest over an edge of the platform 108 reducing, for example, a possibility of melting or otherwise damaging adjacent surgical tools/instruments 117.

Figure 3:
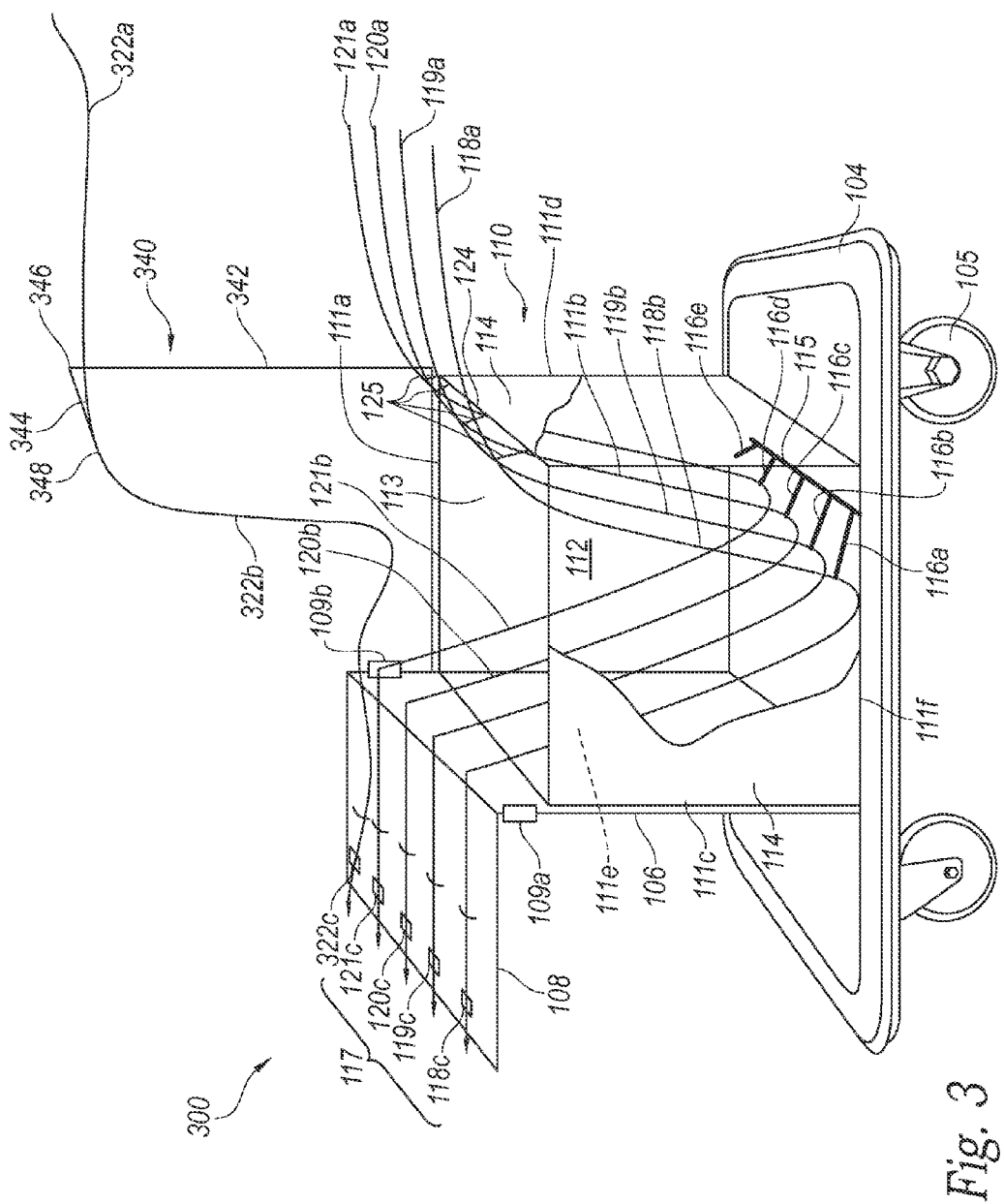
FIG. 3 is a partially schematic isometric view of an instrument organization system configured in accordance with still another embodiment of the present technology.

FIG. 3 is a partially schematic isometric view of an organization system 300 configured in accordance with still another embodiment of the present technology. In this embodiment, the container 110 includes a support system 340 including an arm 342 attached to a coupling member 344 via an elbow joint or hinge 346. The support system 340 can be configured to direct or otherwise guide instruments (e.g., surgical tools, cables, cords, hoses, wires) from an overhead position (e.g., proximate a ceiling of an operating room) toward the platform 108. In the illustrated embodiment, an instrument 322 (e.g., a surgical tool, cable, cord, hose, wire) having a distal portion 322*a*, an intermediate portion 322*b*, and a proximal portion 322*c* can be directed from an overhead location toward the container 110 and the platform 108. The support system 340 can receive the distal portion 322*a* from the overhead location at the coupling member 344 and be attached or fastened thereto with a fastener 348 (e.g., a hook, Velcro strip and/or any other suitable fastener). The support system 340 is configured to guide the intermediate portion 322*b* toward the container 110 and the platform 108. The platform 108 is configured to support and secure the proximal portion 322*c*.

Figure 4A:
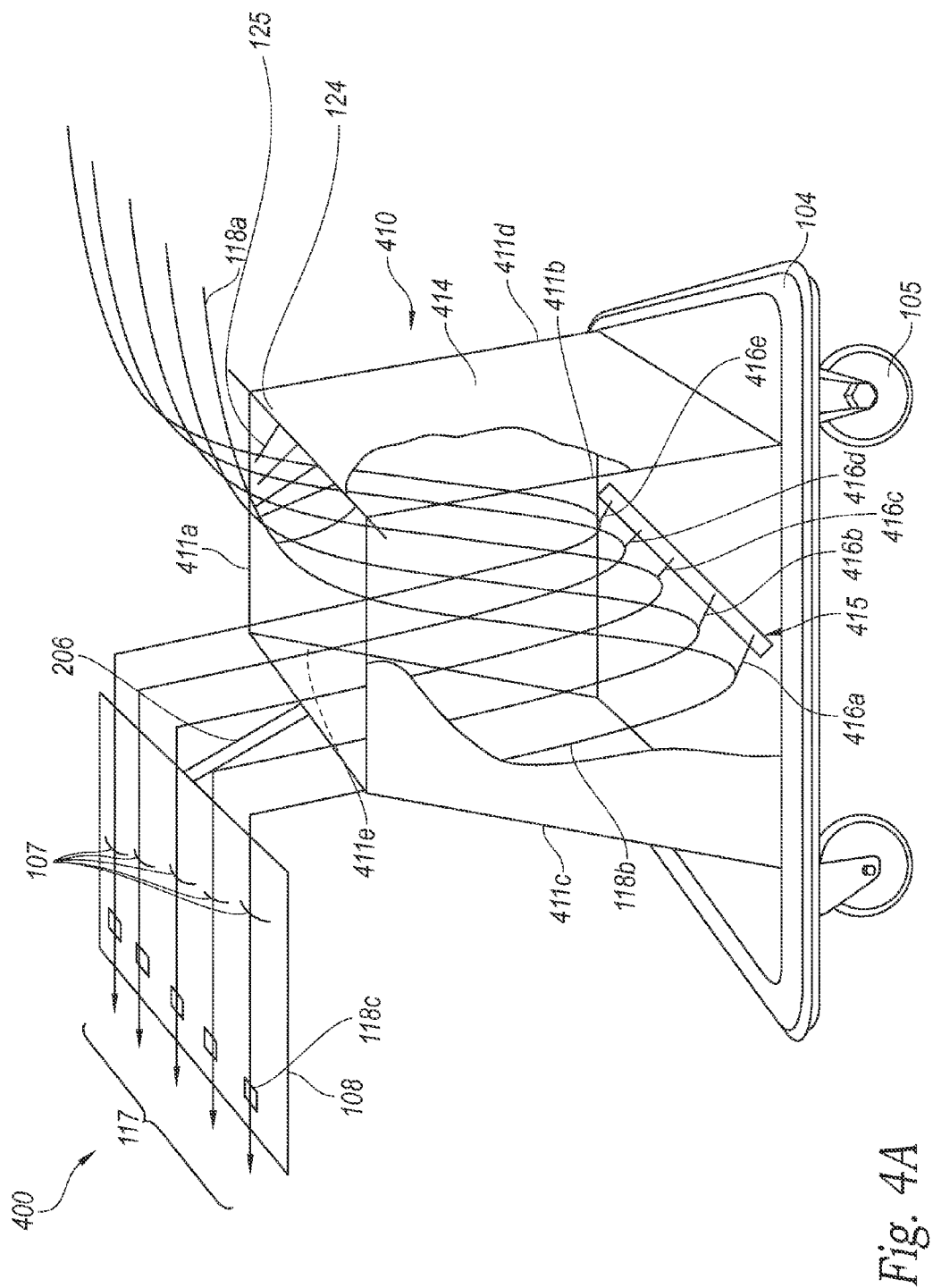
FIG. 4A is a partially schematic isometric view of an instrument organization system configured in accordance with an embodiment of the present technology.

FIG. 4A is a partially schematic isometric view of an organization system 400 configured in accordance with an embodiment of the present technology. In this embodiment, the organization system 400 includes a flexible, sterile container 410 having an upper portion 411*a*, a first side portion 411*b*, a second side portion 411*c*, a third side portion 411*d*, a fourth side portion 411*e* and a lower portion 411*f*. In the illustrated embodiment, the container 410 the side portions 411*b*-411*e* have a generally trapezoidal shape and the lower portion 411*f* has a generally square shape. In other embodiments, however, the side portions 411*b*-411*e* and the lower portion 411*f* can have any suitable shape (e.g., a rectangle, a triangle, a circle, a pentagon, a hexagon and/or any other polygonal shape).

The container 410 comprises a barrier 414 (e.g., similar to the barrier 114 of FIG. 1A or another suitable barrier). An attachment system 415 at the lower portion 411f includes a plurality of tethers 416 (identified individually as a first tether 416a, a second tether 416b, a third tether 416c, a fourth tether 416d, and a fifth tether 416e). Each of the tethers 416 is configured to elastically couple and/or attach a corresponding surgical tool/instrument 117 to the attachment system 415. In one or more alternate embodiments (not shown), the tethers 416 can be included in an attachment system external to the container 410 (e.g., disposed on the base 104). In these embodiments, individual tethers 416 can be attached or otherwise coupled (e.g., fastened by clips) to corresponding instruments 117 through the barrier 414 via by any manner of clips. Moreover, in some embodiments, the container 410 may also include a plurality of individual compartments in which a first compartment (not shown) may be configured to move independently of one or more compartments (not shown) therein when, for example, corresponding instruments 117 are moved (e.g., extended, retracted, and/or replaced).

FIG. 4B is an enlarged view of the attachment system 415 removed from the container 410. The attachment system 415 includes a housing 450 having a plurality of retractors 452 arranged therein. The individual retractors 452 are configured to be attached or otherwise coupled to corresponding tethers 416 via an attachment point 454. Each of the tethers 416 can include a first end configured to be attached to an instrument (e.g., one of the surgical tools/instruments 117) and a second end configured to be attached to a corresponding retractor 452 and at least partially wound therearound. Each of the retractors 452 can have an associated recoil (e.g., a rotational force exerted on a corresponding tether 116). Further, in some embodiments the recoil of the retractors 452 can be collectively and/or individually adjusted by an operator.

Figure 5A:
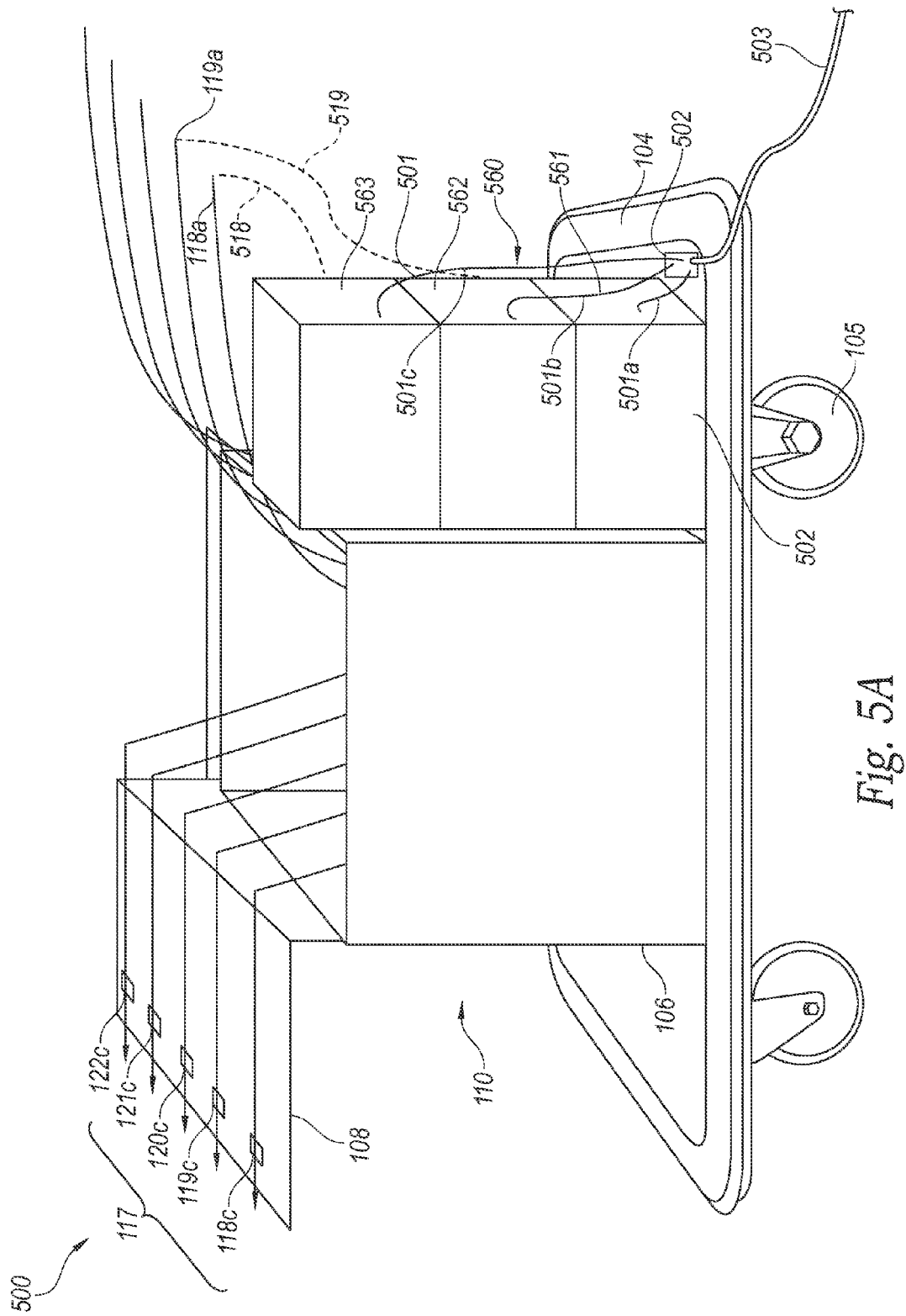
FIG. 5A is a partially schematic isometric view of an instrument organization system configured in accordance with an embodiment of the present technology.

FIG. 5A is a partially schematic isometric view of an instrument organization system 500 configured in accordance with still another embodiment of the present technology. In the illustrated embodiment, the organization system 500 includes a base portion 504 configured to carry or receive both the container 110 and equipment 560. The equipment 560 can include, for example, a plurality of components including a first medical component 561, a second medical component 562, and a third medical component 563. The equipment 560 may also include a power supply 502 (e.g., a power supply having one or more electrical outlets) coupled to an external power source via an electrical cable 503. The power supply 502 is configured to deliver electrical power to the individual medical components 561-563 via electric cables 501a-501c, respectively. The power supply 502 thus allows the components 561-563 to be connected to external power while reducing the number of electrical cables leading from the system 500. While the embodiment shown in FIG. 5A includes a single power supply, in other embodiments, for example, more than one power supply may be used.

As those of ordinary skill in the art will appreciate, the medical components 561-563 can include, for example, instrument control components and/or devices configured to display patient information (e.g., EKG displays, heart rate displays, temperature) The medical components 561-563 can be attached to corresponding surgical tools/instruments 117, thereby connecting the medical components 561-563 to corresponding surgical devices to be used by a doctor or clinician at the operating table. As shown in the illustrated embodiment of FIG. 5A, conduits 518 and 519 (e.g., surgical tools, cables, hoses, wires) can connect the second medical component 562 and the third medical component 563 to corresponding instruments 117.

Figure 5B:
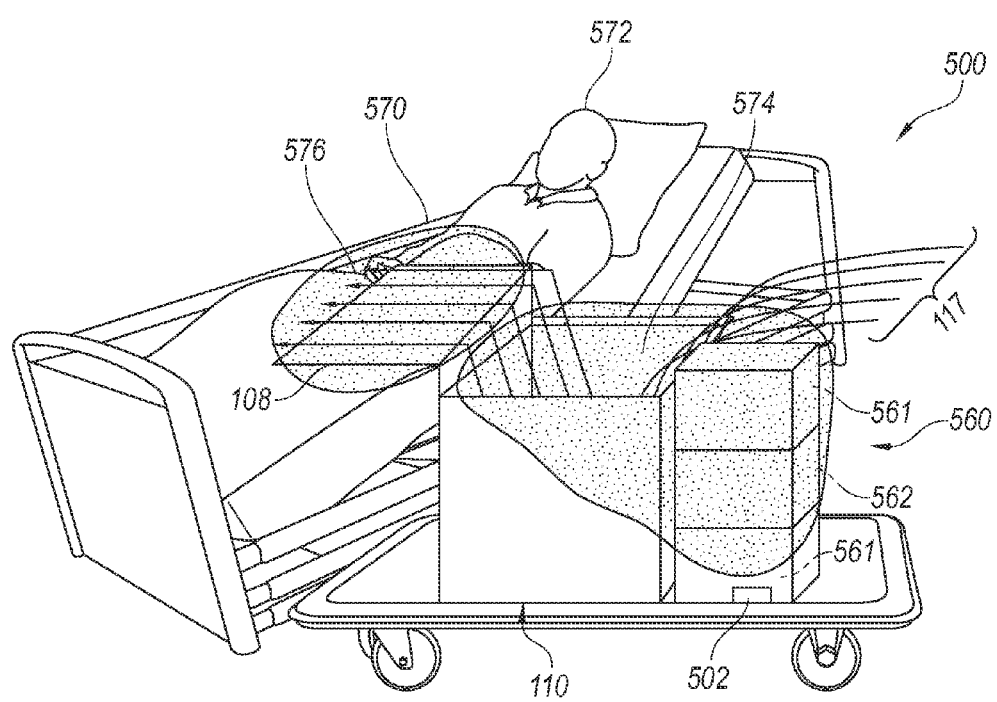
FIG. 5B is perspective view of the organization system of FIG. 5A positioned proximate a patient undergoing treatment.

FIG. 5B is a perspective view of the organization system 500 of FIG. 5A positioned proximate a patient 572 on a table 570 (e.g., an operating table). A first sheath 574 (e.g., a sterile sheet, drape, barrier) can be draped or otherwise positioned on or near at least a portion of the container 110 and/or the equipment 560. A second sheath 576 (e.g., a sterile sheet, drape, barrier) can be draped or otherwise positioned on or near at least a portion of the platform 108 and/or the table 570. The first sheath 574 can be configured, for example, to allow surgical tools/instruments 117 to be received into the container 110 while also providing a sterile barrier for the organization system 500 and the medical components 561-563. The first sheath 574 can also, for example, allow an operator (e.g., a surgeon) to access and/or adjust one or more of the medical components 561-563 without needing assistance from a non-sterile assistance. The second sheath 576 can, for example, allow for sterile placement of instruments 117 on the patient 572 during a surgical procedure. While the embodiment of the organization system 500 shown in FIG. 5B includes the first sheath 574 and the second sheath 576, those of ordinary skill of the art will appreciate that in other embodiments, the organization system 500 can include a single sheath and/or can include three or more sheaths.

Figure 6:
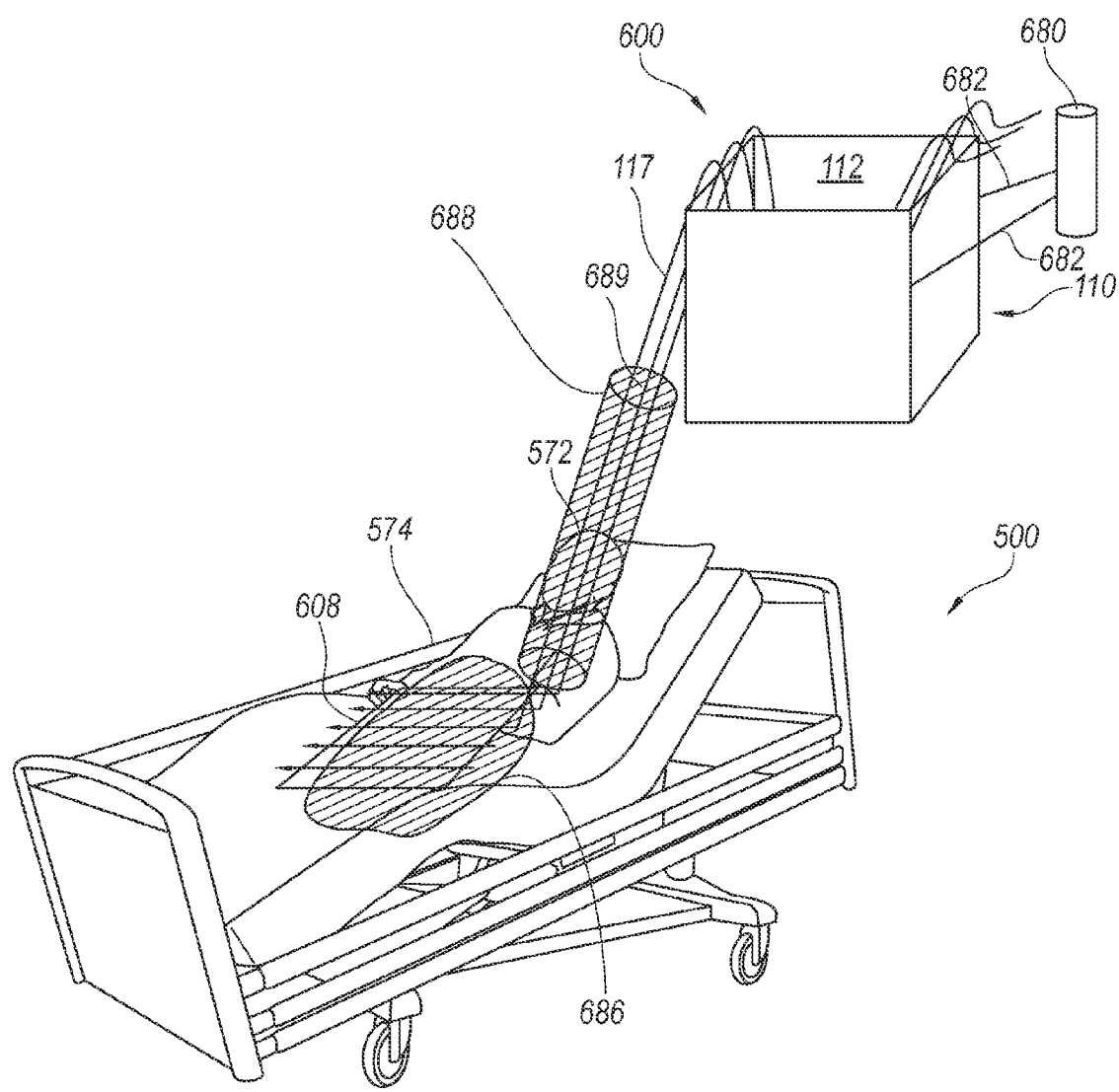
FIG. 6 is a perspective view of an instrument organization system configured in accordance with an embodiment of the present technology.

FIG. 6 is a perspective view of the container 110 from FIG. 1, shown attached to suspended from a room surface 678 (e.g., a ceiling of a hospital room) via an attachment member 680. A plurality of arms 682 attach or otherwise couple the container 110 to the attachment member 680. The attachment member 680 can be configured to rotatably move the container 110 from a first position to a second position. In other embodiments, the attachment member can be configured to move the container 110 from a first height to a second height. The organization system 600 can also include a remote platform 608 positioned at least proximate the patient 572 and can be configured to receive proximal portions of the instruments 117. A sterile sheath 686 can be placed under and/or around the platform 608. A sterile sheath or wrap 688 defining a bore 689 can receive the surgical tools/instruments 117 within the bore 689. The wrap 688 can be made of any suitable sterile material (e.g., polyethylene, nylon, rayon, polyester) and can be configured to surround at least a portion of the surgical tools/instruments 117 between the container 110 and the platform 108. The sheath 686 and the wrap 688 can thus provide a sterile field between the container 110 and the patient 572.

The disclosure may be defined by one or more of the following examples:

1. A surgical instrument organization system, comprising:
   a base;
   a support member fixedly attached to the base;
   a platform operably coupled to the support member; and
   a container attached to the base and the support member, wherein the container includes a lower portion, wherein the container is configured to receive a plurality of surgical instruments, and wherein the container includes an attachment system configured to operably couple surgical instruments to the lower portion of the container.

2. The system of example 1 wherein each of the plurality of surgical instruments includes a distal portion, an intermediate portion and a proximal portion, and wherein the container comprises a flexible, sterile container configured to receive the intermediate portions of the plurality of surgical instruments.

3. The system of example 1 wherein each of the plurality of surgical instruments includes a distal portion, an intermediate portion and a proximal portion, wherein the container comprises a framework that includes the lower portion and a plurality of side portions, and wherein the framework defines a space through which the intermediate portions of the plurality of surgical instruments are received.

4. The system of example 3 wherein at least one of the side portions has a trapezoidal shape.

5. The system of any of examples 1-4, further comprising a first medical component and a second medical component carried by the base proximate the container, wherein the first and second medical components are configured to be electrically connected to a power supply at the base, wherein the plurality of surgical instruments includes a first surgical instrument with a first cable and a second surgical instrument with a second cable, wherein the first medical component is operably coupled to the first surgical instrument, and wherein the second medical component is operably coupled to the second surgical instrument.

6. The system of any of examples 1-5, further comprising a sterile sheath configured to cover at least a portion of the container and the platform.

7. The system of any of examples 1-6 wherein the platform includes a plurality of fasteners positioned to releasably secure a proximal portion of each of the plurality of surgical instruments to the platform.

8. The system of any of examples 1-7 wherein the attachment system comprises a plurality of tethers, and wherein individual tethers are configured to elastically attach corresponding surgical instruments to the container.

9. The system of example 8 wherein the attachment system comprises a plurality of retractors, wherein each of the plurality of tethers comprises a first and a second end, wherein the first end is configured to be attached to an surgical instrument, and wherein the second end is configured to be attached to and at least partially wound around a corresponding retractor.

10. A surgical tool organization system configured for use in a medical environment and comprising a flexible, sterile container having a lower portion, wherein the container is configured to receive two or more surgical tools, and wherein the container includes an attachment system configured to elastically couple surgical tools to the lower portion of the container.

11. The system of example 10, further comprising:
a portable base configured to carry the container; and
a platform coupled to the base by an adjustable support member, wherein the platform is hingedly attached to the support member, and wherein the support member is configured to move the platform between a first height and a second height.

12. The system of example 11 wherein the platform includes a plurality of fasteners positioned to releasably secure proximal portions of corresponding surgical tools to the platform.

13. The system of any of examples 10-12 wherein the attachment system comprises a plurality of tethers, wherein individual tethers are configured to elastically attach corresponding surgical tools to the container.

14. The system of example 13 wherein individual tethers have an adjustable elasticity, and wherein the attachment system is configured to allow a user to adjust the elasticity of the individual tethers.

15. The system of example 13 wherein the attachment system comprises a plurality of retractors, wherein individual tethers include a first end and a second end, wherein the first end is configured to be attached to an intermediate portion of a corresponding surgical tool, and wherein the second end is configured to be attached to and at least partially wound around a corresponding retractor.

16. The system of any of examples 10-15, further comprising a support arm configured to be attached to a room surface and extend therefrom, wherein the container is configured to be operably coupled to the support arm.

17. A surgical instrument organization system, comprising:
a flexible, sterile container having a lower portion, wherein the container includes an attachment system configured to retractably secure one or more surgical instruments to the lower portion of the container;
a portable base configured to carry the container; and
a platform coupled to the base by an adjustable support member, wherein the platform is operably coupled to the support member, and wherein the support member is configured to move the platform between a first height and a second height.

18. The system of example 17 wherein the platform is operably coupled to the support member by independently-adjustable first and second coupling devices, wherein the first and second coupling devices are configured to allow a user to adjust an orientation of the platform relative to the base from a first angle to at least a second angle in a first direction.

19. The system of example 18 wherein the first and second coupling devices are configured to allow a user to adjust the orientation of the platform relative to the base from a third angle to at least a fourth angle in a second direction different from the first direction.

20. The system of any of examples 17-19, further comprising means for illuminating the platform.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the

We claim:

1. A surgical instrument organization system, comprising:
   a base;
   a support member fixedly attached to the base;
   a platform operably coupled to the support member; and
   a container attached to the base and the support member, wherein the container is configured to receive a plurality of surgical instruments, and wherein the container includes an attachment system configured to operably couple surgical instruments to a lower portion of the container, and further wherein the support member is configured to move the platform between a first height and a second height above the lower portion of the container, the second height being greater than the first height.

2. The system of claim 1 wherein each of the plurality of surgical instruments includes a distal portion, an intermediate portion and a proximal portion, and wherein the container comprises a flexible, sterile container configured to receive the intermediate portions of the plurality of surgical instruments.

3. The system of claim 1 wherein each of the plurality of surgical instruments includes a distal portion, an intermediate portion and a proximal portion, wherein the container comprises a framework that includes the lower portion and a plurality of side portions, and wherein the framework defines a space through which the intermediate portions of the plurality of surgical instruments are received.

4. The system of claim 3 wherein at least one of the side portions has a trapezoidal shape.

5. The system of claim 1, further comprising a first medical component and a second medical component carried by the base proximate the container, wherein the first and second medical components are configured to be electrically connected to a power supply at the base, wherein the plurality of surgical instruments includes a first surgical instrument with a first cable and a second surgical instrument with a second cable, wherein the first medical component is operably coupled to the first surgical instrument, and wherein the second medical component is operably coupled to the second surgical instrument.

6. The system of claim 1, further comprising a sterile sheath configured to cover at least a portion of the container and the platform.

7. The system of claim 1 wherein the platform includes a plurality of fasteners positioned to releasably secure a proximal portion of each of the plurality of surgical instruments to the platform.

8. The system of claim 1 wherein the attachment system comprises a plurality of tethers, and wherein individual tethers are configured to elastically attach corresponding surgical instruments to the container.

9. The system of claim 8 wherein the attachment system comprises a plurality of retractors, wherein each of the plurality of tethers comprises a first and a second end, wherein the first end is configured to be attached to an surgical instrument, and wherein the second end is configured to be attached to and at least partially wound around a corresponding retractor.

10. A surgical tool organization system configured for use in a medical environment and comprising:
    a flexible, sterile container having a lower portion, wherein the container is configured to receive two or more surgical tools, and wherein the container includes an attachment system configured to elastically couple surgical tools to the lower portion of the container;
    a portable base configured to carry the container; and
    a platform coupled to the base by an adjustable support member, wherein the platform is hingedly attached to the support member,
    wherein the support member is configured to move the platform between a first height and a second height.

11. The system of claim 10 wherein the platform includes a plurality of fasteners positioned to releasably secure proximal portions of corresponding surgical tools to the platform.

12. The system of claim 10 wherein the attachment system comprises a plurality of tethers, wherein individual tethers are configured to elastically attach corresponding surgical tools to the container.

13. The system of claim 12 wherein the attachment system comprises a plurality of retractors, wherein individual tethers include a first end and a second end, wherein the first end is configured to be attached to an intermediate portion of a corresponding surgical tool, and wherein the second end is configured to be attached to and at least partially wound around a corresponding retractor.

14. A surgical instrument organization system, comprising:
    a flexible, sterile container having a lower portion, wherein the container includes an attachment system configured to retractably secure one or more surgical instruments to the lower portion of the container;
    a portable base configured to carry the container; and
    a platform coupled to the base by an adjustable support member, wherein the platform is operably coupled to the support member, and wherein the support member is configured to move the platform between a first height above the lower portion of the container and a second height above the lower portion of the container, wherein the second height is greater than the first height.

* * * * *